United States Patent [19]

Gregory et al.

[11] Patent Number: 5,759,482
[45] Date of Patent: Jun. 2, 1998

[54] WATER COOLED FLUE GAS SAMPLING DEVICE

[75] Inventors: David Scott Gregory, Sour Lake, Tex.; Daniel K. Ferguson, Chicago, Ill.

[73] Assignee: Air Liquide America Corp., Houston, Tex.

[21] Appl. No.: 689,168

[22] Filed: Aug. 7, 1996

[51] Int. Cl.$^6$ .................................................. C21B 7/24
[52] U.S. Cl. ........................................ 266/79; 266/80
[58] Field of Search ............................. 266/79, 80, 81; 373/2

[56] References Cited

U.S. PATENT DOCUMENTS

| 5,166,950 | 11/1992 | Jouvaud et al. | 373/2 |
| 5,344,122 | 9/1994 | Vuillermoz et al. | 266/79 |
| 5,373,530 | 12/1994 | Perrin | 373/2 |

FOREIGN PATENT DOCUMENTS

| 0983496 | 12/1982 | U.S.S.R. | 266/79 |

*Primary Examiner*—Scott Kastler
*Attorney, Agent, or Firm*—Burns, Doane, Swecker & Mathis, L.L.P.

[57] ABSTRACT

A device for sampling flue gas from a duct includes a casing tube having a longitudinal axis, and a port for connecting an interior of the casing tube with a source of cooling fluid, an extraction tube having an end part disposed in the interior of the casing tube, an end of the extraction tube extending through the casing tube to form an inlet opening, an intermediate tube disposed between the casing tube and the extraction tube and spaced from the casing tube and the extraction tube to define a cooling fluid circuit and a sampling tube extending in an interior of the extraction tube and having an opening in an interior of the extraction tube.

19 Claims, 1 Drawing Sheet

WATER COOLED FLUE GAS SAMPLING DEVICE

The invention relates to a device for removing gas samples from a heat process apparatus, for example, a furnace for heat treating or melting materials. More particularly, the invention is directed to a water-cooled, tubular device that is insertable in a duct of a furnace to extract flue gas from the duct.

BACKGROUND AND SUMMARY

U.S. Pat. No. 5,166,950 and U.S. Pat. No. 5,373,530, the disclosures of which are also incorporated herein, describe systems for melting scrap metal in a furnace for steel production. In these systems, a scrap metal charge in the furnace is melted by electric arc energy brought to the charge and by heat generated by post-combustion of CO- and $H_2$-containing fumes produced during melting. Post combustion is achieved by injecting oxygen or oxygen-containing gas into the furnace gases. The use of post combustion heat advantageously reduces the amount of expensive electric arc energy needed for melting the charge. U.S. patent application Ser. No. 08/555,725, filed Nov. 9, 1995, also incorporated herein, discloses a process for melting and refining scrap metal that uses electric arc energy and post combustion heat both for melting the charge, and during the refining step.

In these systems, it is desirable to monitor the flue gases, that is, the gases exhausted from the furnace, as a check on the post combustion process and to use that data for controlling the flow of oxygen or oxygenated gas into the furnace. By sampling the flue gas content, for example, the amount of CO, it may be determined if a sufficient amount of oxygen-containing gas is being injected in the furnace for the desired combustion.

Sampling of such flue gases poses difficulties because the flue gases in these furnaces can exceed 1600° C., and are often highly loaded with metallic dust and water.

U.S. Pat. No. 5,344,122 describes a device and system for sampling and analyzing flue gases that includes a water-cooled probe inserted in a duct of a furnace flue to withdraw a gas sample. This device includes an inner sampling tube surrounded by a cooling casing formed by an outer tube and an intermediate tube defining a cooling fluid flow circuit. The sample is drawn by suction through the inner tube, and a cooling fluid is circulated in the flow circuit around the inner tube to cool the device.

This sampling device is subject to plugging, and must be frequently blown out for cleaning or removed and replaced. The plugs are believed to result from a mass formed by a mixture of condensation, formed as the gas sample cools by contact with the inner tube, and dust carried in the gas. The mass collects and hardens in the sampling tube, blocking the gas sample path. Attempts to prevent condensation and dust mass formation include lowering the cooling water flow, however, the accompanying decrease in cooling of the device results in the earlier onset and increased amount of heat-related damage, which shortens the life of the device.

The present invention provides a sampling device for flue gas monitoring that overcomes this problem. A water-cooled sampling device in accordance with the invention includes a sampling tube for removing gas samples from a duct and an extraction tube that surrounds the sampling tube to provide a protective sleeve with a gas layer surrounding the sampling tube. A cooling jacket surrounds the extraction tube, and a cooling fluid flow in the jacket protects the device from exposure to the hot gas in the duct. The gas layer insulates the sampling tube from the effects of cooling of the extraction tube, and thus inhibits condensation occurring in the sample gas in the sampling tube.

According to a preferred embodiment of the invention, a cooling jacket is formed by an outer casing tube and an intermediate tube. Cooling fluid flows in a circuit in the space between the outer casing tube and the intermediate tube and in the space between the intermediate tube and the extraction tube. The cooling fluid carries heat from the outer casing tube and extraction tube to prevent damage from exposure to the hot gases in the duct. The extraction tube is contacted and cooled by the cooling fluid, but the sampling tube is not in direct contact with cooling fluid, and the opportunity for condensation to form in the gas in the sampling tube is thus avoided.

According to another aspect of the invention, an inlet opening of the sampling tube is spaced from the inlet opening of the extraction tube which provides an entry space that allows the annular space between the extraction tube and the sample tube to fill with gas to form the insulating layer.

According to another aspect of the invention, the extraction tube is disposed in the intermediate tube and extends through the intermediate tube and casing tube to form an inlet opening. An end portion of the extraction tube is shaped as an elbow so that the inlet of the extraction tube is formed on the side of the casing tube and oriented substantially perpendicular to a longitudinal axis of the casing tube. With this arrangement, the device may be inserted in a duct so that the inlet opening is substantially in counterflow to the direction of gas flow in the duct.

BRIEF DESCRIPTION OF THE DRAWINGS

The invention may be better understood through the following description in conjunction with the appended drawings, in which like elements are identified by reference characters, and wherein.

DETAILED DESCRIPTION

The invention is related to an apparatus for withdrawing and analyzing a gas sample taken from a heat treating or melting furnace as described in U.S. Pat. No. 5,344,122, which is incorporated herein by reference. In that system, a gas sample is drawn from the furnace flue, and passed through a water condenser, a drier, and a dust filter before being sent to gas analyzer devices. In the gas analyzers, the cleaned flue gas is checked for carbon monoxide, carbon dioxide, and hydrogen. Data from the gas analyzers is sent to a central processing unit, which also receives a signal indicating the temperature of the flue gas. The central processing unit controls a regulator device for the flow of oxygen or oxygenated gas into the furnace. The central processing unit may be programmed for the different stages of the process, the initial melting and the refining, for example, which require different quantities of heat.

Figure 1:
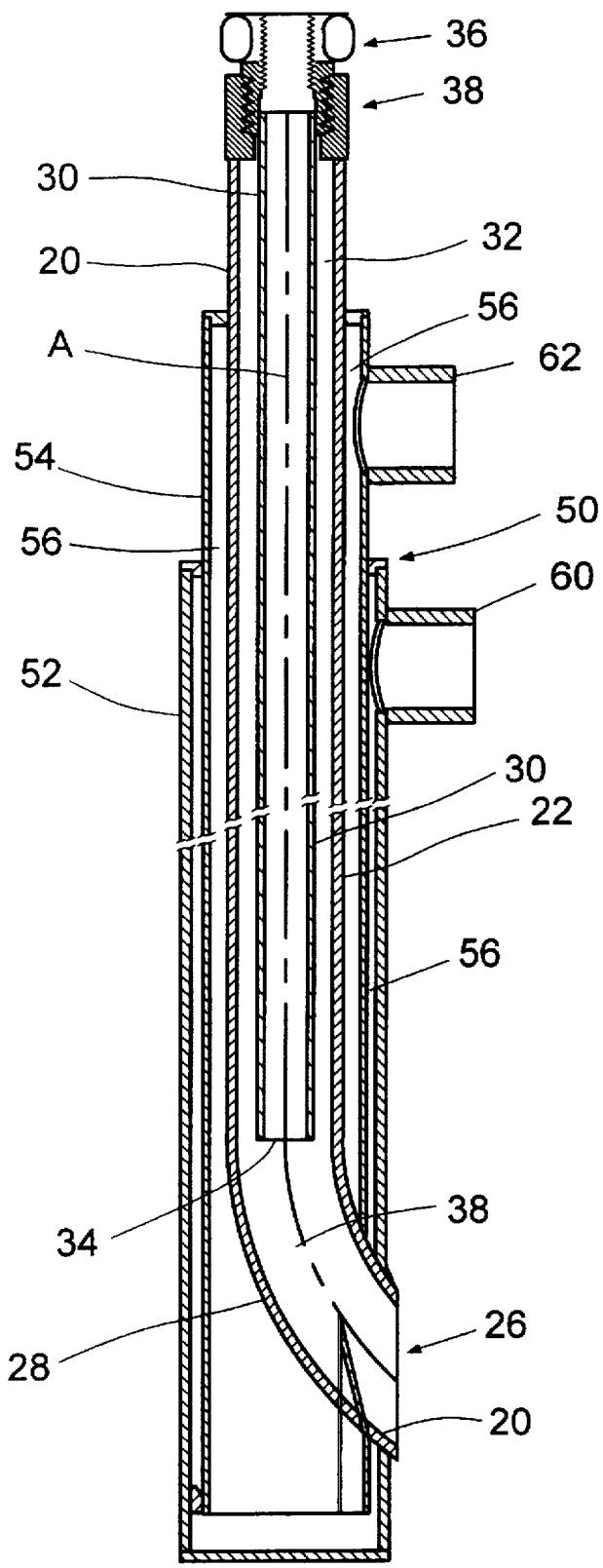
FIG. 1 is a sectional view of a sampling device in accordance with the invention; and, FIG. 2 is a view of an alternative embodiment of an inlet end of a sampling device in accordance with the invention.

FIG. 1 shows a longitudinal sectional view of a gas sampling device in accordance with the invention. The device comprises an elongated tubular structure having a longitudinal axis A. The device is insertable in a duct to withdraw a gas sample from the duct. An extraction tube 20 includes an insertion portion 22 protected by cooling jacket means 50, which is positioned in the gas flow to draw gas from the duct. The extraction tube 20 has an inlet opening 26 through which gas or fumes are drawn into the device. A sampling tube 30 disposed in the extraction tube 20 removes a gas sample from the extraction tube 20.

As mentioned, the flue gas may be at a temperature in excess of 1600° C., which requires cooling to prevent the damage to the device. The cooling jacket means 50 provides a protective sleeve and a cooling fluid circuit around the extraction tube 20.

In the illustrated embodiment, the cooling jacket means 50 includes a casing tube 52 forming an outermost sleeve member and an intermediate tube 54 mounted to extend in the casing tube between the casing tube and the extraction tube 20. The intermediate member 54 is spaced from both the casing tube 52 and the extraction tube 20 to define a cooling fluid flow circuit 56 including an outer annular space between the casing tube and the intermediate tube and an inner annular space between the intermediate tube and the extraction tube. The casing tube 52 includes an inlet stub 60 to connect with a source for circulating cooling water (not illustrated), and the intermediate tube 54 is connected to an outlet stub 62 to connect with the cooling water source. As may be understood by reference to FIG. 1, cooling water flowing in through the inlet stub 60 flows in the outer part of the flow circuit 56 to contact and cool the casing tube 52 and then to the inner portion of the circuit to cool the extraction tube 20 before flowing out of the outlet stub 64.

The extraction tube 20 includes an elbow-shaped portion 28 adjacent the inlet opening 26 which extends through the side walls of the intermediate tube 54 and the casing tube 52 to form the inlet opening 26 on the wall of the casing tube. The inlet opening 26 is substantially perpendicular to the longitudinal axis A of the device. When the device is inserted in a duct, the inlet opening 26 is substantially coaxial with the flow direction of the duct, and may be oriented to be in counterflow with the flow in the duct. According to a preferred embodiment, the radius of curvature of the elbow is at least three times the diameter of the extraction duct 20.

Figure 2:
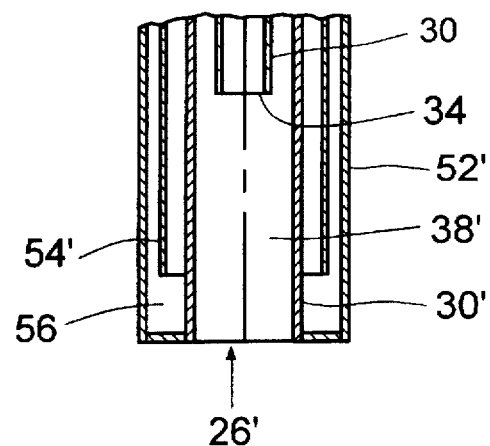

Alternatively, as illustrated in FIG. 2, the extraction tube 30' may extend to the longitudinal end of the casing tube 52' to form an inlet opening 26' at the longitudinal end of the device.

A sampling tube 30 is mounted in the extraction tube 20 and spaced from the extraction tube so that an annular space 32 surrounds the sampling tube. The sampling tube 30 is not contacted by cooling fluid. The sampling tube 30 includes an opening 34 that is disposed in the extraction tube 20 to remove gas from the extraction tube.

The sampling tube 30 may be connecting to a pump apparatus to produce suction to withdraw gas and devices to analyze the gas as described in U.S. Pat. No. 5,344,122. A coupling collar 36 connects the sampling tube 30 to a collecting and analyzing apparatus. The sampling tube 30 is connected to the extraction tube 20 by threaded fastening means 38.

As shown in the embodiments of FIG. 1 and FIG. 2, the opening 34 of the sampling tube 30 is spaced from the inlet opening 26, 26' of the extraction tube to provide an entry area 38, 38'. The sampling tube 30 is thus protected from direct contact with the hot gas flow in the duct. The space ensures a low gas velocity at the opening 34 of the sampling tube 30, which minimizes the amount of dust that enters the sampling tube.

When the device is positioned in a duct, the annular space 32 around the sampling tube 30 fills with gas from the duct and a stagnant gas layer forms. Because of the low thermal conductivity of gas, the stagnant annular layer of gas insulates the sampling tube from the effects of the cooling water circuit 56 outside the extraction tube 20. The opportunity for condensation to occur in the gas in the sampling tube 30 is therefore minimized or eliminated. Accordingly, the formation of a dust/condensation mass and plug formation is avoided. Further, because the insulating layer of gas in the annular space 32 is stagnant, the accumulation of a dust and condensation mass in this space 32 and the resultant plugging here is also minimized.

In the embodiment of FIG. 1, the inlet opening 26 is disposed in counterflow to the duct flow direction, and the gas changes direction to enter the extraction tube 20 and again to enter the sampling inlet 34, which minimizes the amount of dust which can follow the gas.

The device is formed of a material or materials capable of withstanding the severe temperature and corrosive conditions in the flue gas, and may be made of stainless steel, a ceramic, or other suitable materials.

The invention has been described in terms of preferred principles, embodiments and modes of operation. The invention should not be construed as limited to the particular embodiments described. Instead, the above-described embodiments should be regarded as illustrative and not restrictive, and variations, changes and equivalents may be made by others without departing from the scope of the invention as defined by the following claims.

What is claimed is:

1. A device for sampling gas from a duct, comprising:
    an extraction tube having an end portion for insertion in a gas duct, the end portion having an inlet opening;
    cooling jacket means surrounding the insertion portion to circulate a flow of cooling fluid to an outer surface of the extraction tube, the outer surface of the extraction tube providing a closed wall for the cooling jacket so that no cooling fluid flows in an interior of the extraction tube; and
    a sampling tube mounted in the extraction tube and spaced from an interior surface of the extraction tube, the sampling tube having an opening to collect a gas sample.

2. The device as claimed in claim 1, wherein the opening of the sampling tube is positioned in an interior of the extraction tube spaced from the inlet opening.

3. The device as claimed in claim 1, wherein the opening of the sampling tube is positioned proximate to the inlet opening.

4. The device as claimed in claim 1, wherein the cooling jacket means comprises a casing tube having a longitudinal axis and having means for connecting an interior of the casing tube with a source of cooling fluid, and an intermediate tube disposed between the casing tube and the extraction tube and spaced from the casing tube and the extraction tube to define a cooling fluid circuit.

5. The device as claimed in claim 4, wherein the intermediate tube includes means for connecting an interior of the intermediate tube with the cooling fluid source.

6. The device as claimed in claim 4, wherein the inlet opening is arranged coaxially with the casing tube axis.

7. The device as claimed in claim 4, wherein the inlet opening is arranged substantially perpendicular to the casing tube axis.

8. The device as claimed in claim 7, wherein an end portion of the extraction tube adjacent the inlet opening is elbow-shaped.

9. The device as claimed in claim 8, wherein the sample tube opening is disposed at an end of the elbow-shaped portion opposite the inlet opening.

10. The device as claimed in claim 8, wherein the elbow-shaped portion of the extraction tube has a radius of curvature that is at least three times a diameter of the extraction tube.

11. The device as claimed in claim 1, wherein a portion of the extraction tube adjacent the inlet opening is elbow-shaped.

12. A device for sampling fumes from a duct, comprising:
- a casing tube having a longitudinal axis, and having means for connecting an interior of the casing tube with a source of cooling fluid;
- an extraction tube having an end part disposed in the interior of the casing tube, an end of the extraction tube extending through the casing tube to form an inlet opening;
- an intermediate tube disposed between the casing tube and the extraction tube and spaced from the casing tube and the extraction tube to define a cooling fluid circuit; and
- a sampling tube extending in an interior of the extraction tube and having an opening in an interior of the extraction tube 13.

13. The device as claimed in claim 12, wherein the sample tube opening is spaced from the inlet opening.

14. The device as claimed in claim 12, wherein the inlet opening is arranged coaxially with the casing tube axis.

15. The device as claimed in claim 12, wherein the inlet opening is arranged substantially perpendicular to the casing tube axis.

16. The device as claimed in claim 15, wherein an end portion of the extraction tube adjacent the inlet opening is elbow-shaped.

17. The device as claimed in claim 16, wherein the elbow-shaped portion of the extraction tube has a radius of curvature that is at least three times a diameter of the extraction tube.

18. The device as claimed in claim 16, wherein the sample tube opening is disposed at an inner end of the elbow-shaped portion opposite the inlet opening.

19. The device as claimed in claim 12, wherein the intermediate tube includes means for connecting an interior of the intermediate tube with the cooling fluid source.

* * * * *

UNITED STATES PATENT AND TRADEMARK OFFICE
CERTIFICATE OF CORRECTION

PATENT NO. : 5,759,482
DATED     : JUN. 2, 1998
INVENTOR(S) : GREGORY ET AL.

It is certified that error appears in the above-identified patent and that said Letters Patent is hereby corrected as shown below:

In Claim 12, line 25, after the word "tube", please delete --13--.

Signed and Sealed this

Twenty-second Day of September, 1998

Attest:

BRUCE LEHMAN

*Attesting Officer*          *Commissioner of Patents and Trademarks*